(12) United States Patent
Margolin et al.

(10) Patent No.: US 8,093,210 B2
(45) Date of Patent: Jan. 10, 2012

(54) TREATMENT OF SEPSIS WITH 5-ETHYL-1-PHENYL-2(1H)-PYRIDONE

(75) Inventors: Solomon B. Margolin, Dallas, TX (US); Shri N. Giri, legal representative, Dallas, TX (US); Shri N. Giri, Addison, TX (US)

(73) Assignee: Solanan, Inc., Dallas, TX (US)

( * ) Notice: Subject to any disclaimer, the term of this patent is extended or adjusted under 35 U.S.C. 154(b) by 0 days.

(21) Appl. No.: 12/921,107

(22) PCT Filed: Mar. 9, 2009

(86) PCT No.: PCT/US2009/036529
§ 371 (c)(1),
(2), (4) Date: Sep. 3, 2010

(87) PCT Pub. No.: WO2009/111785
PCT Pub. Date: Sep. 11, 2009

(65) Prior Publication Data
US 2011/0092549 A1 Apr. 21, 2011

Related U.S. Application Data

(60) Provisional application No. 61/096,132, filed on Sep. 11, 2008, provisional application No. 61/034,614, filed on Mar. 7, 2008.

(51) Int. Cl.
*A61K 38/00* (2006.01)
*A61K 31/445* (2006.01)
*C07D 211/72* (2006.01)

(52) U.S. Cl. .......... 514/1.4; 514/345; 424/643; 546/290

(58) Field of Classification Search .................... 514/1.4, 514/345; 546/290; 424/643
See application file for complete search history.

(56) References Cited

U.S. PATENT DOCUMENTS

| 6,300,349 B1 | 10/2001 | Margolin |
| 2008/0025986 A1 | 1/2008 | Ozes |

FOREIGN PATENT DOCUMENTS

| JP | 06-226090 A | 8/1994 |
| WO | WO 9947140 A1 | 9/1999 |
| WO | WO 2005/000227 | * 1/2005 |
| WO | WO 2005038056 A1 | 4/2005 |

OTHER PUBLICATIONS

Cain, William C. "Therapeutic Use of Pirfenidone Against Septic Shock," Master of Science Thesis Texas Tech University. Dated Aug. 1997, publication date unknown.

(Continued)

*Primary Examiner* — Jeffrey S. Lundgren
*Assistant Examiner* — Savitha Rao
(74) *Attorney, Agent, or Firm* — Eugenia S. Hansen; Hemingway & Hansen, LLP

(57) ABSTRACT

A pharmaceutical composition comprising 5-ethyl-1-phenyl-2-(1H)-pyridone (5-EPP) and its use for the treatment of sepsis are disclosed.

12 Claims, 3 Drawing Sheets

OTHER PUBLICATIONS

Wichterman, et al. 1980. "Sepsis and Septic Shock—A Review of Laboratory Models and a Proposal," Journal of Surgical Research 29:189-201.

Bruss, et al. 2008. "Pharmacokinetics and Metabolism of Intravenous Pirfenidone in Sheep," Biolphamraceutics & Drug Disposition 29:119-126.

Braim, et al. 2009. "Effects of intravenous administration of pirfenidone on horses with experimentally induced endotoxemia," AJVR vol. 70, No. 8, 1031-1042.

Garretson S, Malberti S. 2007. "Understanding hypovolaemic, cardiogenic and septic shock," Nursing Standard 21 (50): 51-54.

* cited by examiner 5-ethyl-1-phenyl-2-(1H)-pyridone ("5-EPP")

TREATMENT OF SEPSIS WITH 5-ETHYL-1-PHENYL-2(1H)-PYRIDONE

CROSS REFERENCE TO RELATED APPLICATIONS

This application claims the benefit of U.S. provisional applications 61/034,614 filed Mar. 7, 2008 and 61/096,132 filed Sep. 11, 2008.

TECHNICAL FIELD

This invention relates to a pyridone compound, 5-ethyl-1-phenyl-2-(1H)-pyridone, new processes for its synthesis and purification, pharmaceutical compositions containing it and its use in the treatment of sepsis.

DETAILED DESCRIPTION

A compound, 5-ethyl-1-phenyl-2-(1H)-pyridone and new methods of making it, purifying it, employing it in a pharmaceutical composition for the treatment of sepsis, and using it is herein described.

Although the chemical structure of 5-ethyl-1-phenyl-2-(1H)-pyridone has been named in prior patents and literature, heretofore there has been no known disclosure of an effective way to make and purify this compound.

Effective synthesis methods for 5-ethyl-1-phenyl-2-(1H)-pyridone from a starting compound, 3-ethyl pyridine, are now provided.

Figure 1:
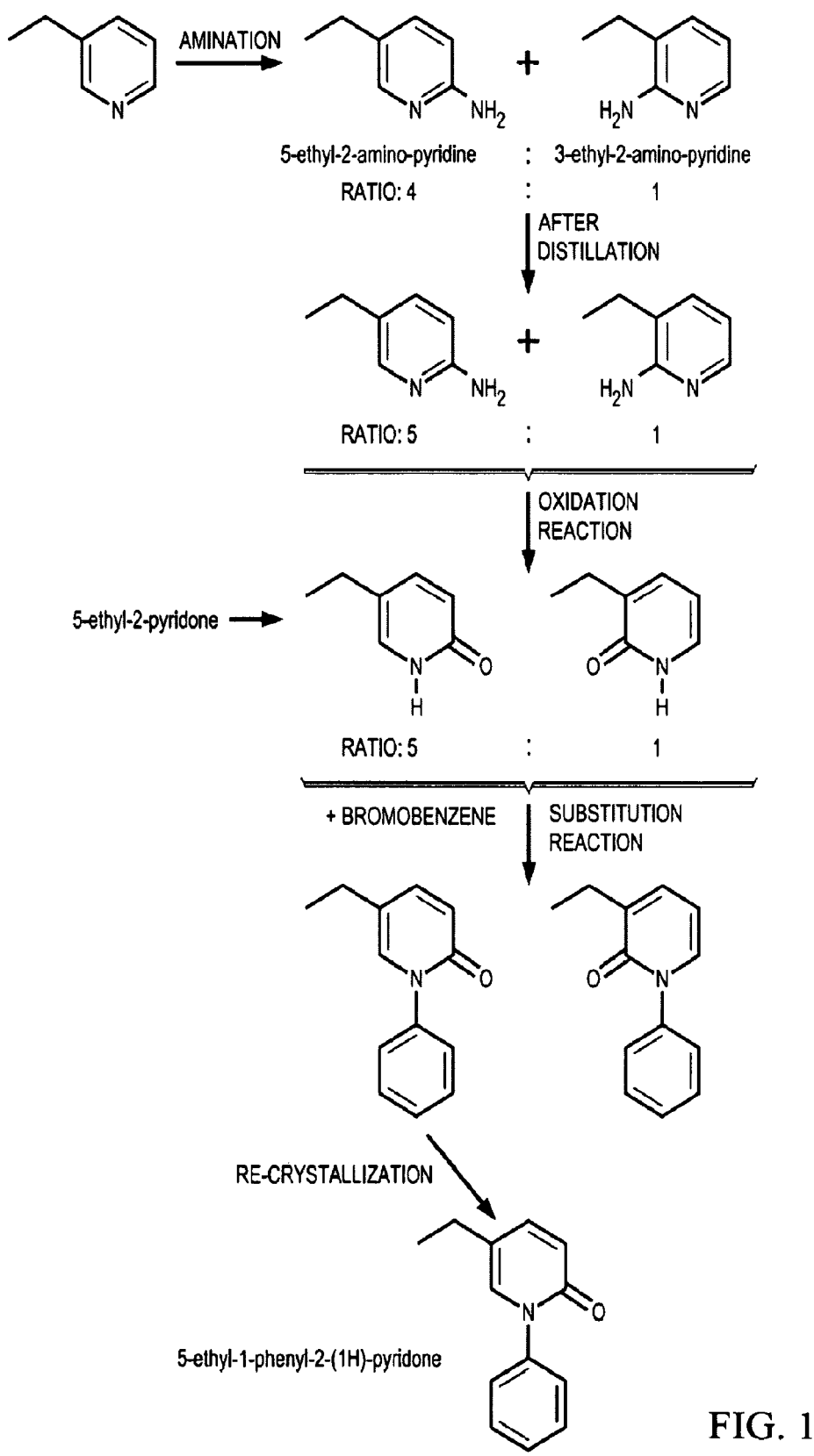
FIG. 1 is a schematic synthesis scheme for 5-ethyl-1-phenyl-2-(1H)-pyridone ("5-EPP")

A first reaction scheme useful for synthesis of 5-ethyl-1'-phenyl-2-(1H) pyridone is provided in FIG. 1.

In said first reaction scheme, we have found that 5-ethyl-1-phenyl-2-(1H)-pyridone can be made from 3-ethyl pyridine (available from Sigma-Aldrich Corporation, St. Louis, Mo.) which is reacted with $NaNH_2$ in presence of a small amount of oleic acid as a catalyst to speed up the reaction. A general reaction scheme for obtaining 2-amino-5-ethyl pyridine isomer from 3-ethylpyridine is provided in U.S. Pat. No. 5,003,069 to McGill et al, "Chichibabin Reaction," at Example 12. U.S. Pat. No. 5,003,069 is herein incorporated by reference as if fully set forth herein. In this reaction 3-ethyl pyridine (I) is converted to 2-amino-5-ethylpyridine (II) as well as 2-amino-3-ethylpyridine(III).

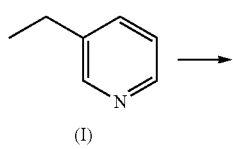

(I)

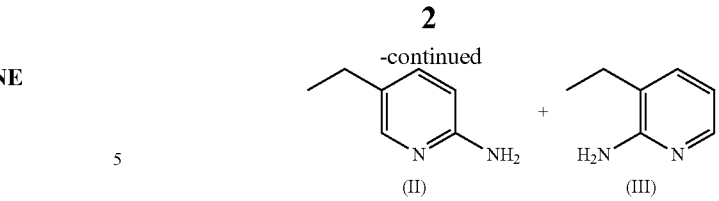

After repeated distillation, the desired isomer, 2-amino-5-ethyl pyridine (Structure II, above) is obtained.

We have found that 2-amino-5-ethyl pyridine can be converted to the desired product, 5-ethyl-1-phenyl-2-(1H)-pyridone. In the procedure of the invention, 2-amino-5-ethyl pyridine isomer is first oxidized to form 5-ethyl-2-pyridone.

In the preferred oxidation method of the invention, 2-amino-5-ethyl pyridine is dissolved in 20% sulfuric acid ($H_2SO_4$, wt/vol) and chilled thoroughly in an ice bath. A preferred reactant, sodium nitrite ($NaNO_2$, wt/vol, 1.2 mole equivalents) solution is then added over 4-5 hours to oxidize 2-amino-5-ethyl pyridine into 5-ethyl-2-pyridone.

After oxidation, $Na_2CO_3$ (2.0 mole equivalents) is added to the reaction mixture until a pH=8-8.5 is attained, and a two-phase mixture dark yellow upper organic phase and a lower light yellow aqueous phase is obtained.

The aqueous phase is extracted with methylene chloride ($CH_2Cl_2$) and pooled with the organic phase. After drying, a light yellow solid is obtained which is 5-ethyl-2-pyridone.

A substitution reaction is then conducted in order to substitute a phenyl group on the N of the pyridone ring of 5-ethyl-2-pyridone for the hydrogen. The 5-ethyl-2-pyridone is preferably reacted in the presence of a copper-zinc catalyst and potassium carbonate with a halobenzene. Preferably the halobenzene is selected from iodobenzene and bromobenzene. Most preferably, bromobenzene is utilized. 5-ethyl-1-phenyl-2-(1H)-pyridone is formed and will be in the reaction mixture.

The method of the invention includes purification of the 5-ethyl-1-phenyl-2-(1H)-pyridone from the reaction mixture. After completion of the reaction, as ascertained by thin layer chromatography (TLC), un-reacted bromobenzene was removed by distillation under high vacuum.

The remaining solution was extracted with $CH_2Cl_2$. The extract was vacuum filtered through a short Celite column to remove any small particles.

The above extract was treated with activated charcoal and boiled for 10-15 minutes, then cooled to room temperature before removing the charcoal by vacuum filtration through a second Celite column.

The volume of filtrate was reduced by rotary evaporation. The resulting oily concentrate was dried at room temperature to yield a dark-brown solid which contained 75% 5-ethyl-1-phenyl-2-(1H)-pyridone.

The dark-brown solid was first dissolved in warm ethyl acetate and then boiled. Hexane was added to the boiling solution and continuously stirred to separate the upper phase (hexane-rich) from the lower phase (ethyl acetate).

The upper phase was poured into a beaker and allowed to cool and settle first, then transferred to a Teflon coated pan.

After evaporation and cooling, white 5-ethyl-1-phenyl-2-(1H)-pyridone crystals formed throughout the pan.

The purified white crystals after drying yielded a fine white crystalline powder with a melting point of 57-59° C.

Reverse phase HPLC analysis and NMR revealed the powder contained >99% 5-ethyl-1-phenyl-2-(1H) pyridone.

In a second reaction scheme, a one-step synthesis method for making the compound 5-ethyl-1-phenyl-2-(1H)-pyridone has also been developed. The first reaction scheme discussed above involves a three step process.

Second Reaction Scheme:

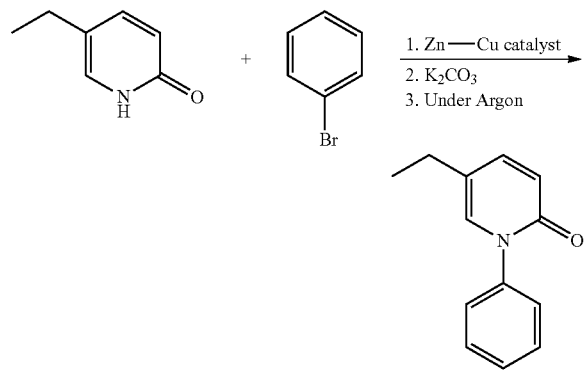

We have found that 5-ethyl-1-phenyl-2-(1H)-pyridone can be made from the starting material, 5-ethyl-2-pyridone (J & W Pharlab LLC, Levitton, Pa.). 5-ethyl-2-pyridone is reacted with bromobenzene in the presence of a Cu—Zn catalyst under a blanket of argon to produce 5-ethyl-1-phenyl-2-(1H)-pyridone.

Preparation of Catalyst: A copper-zinc (Cu—Zn) catalyst was prepared immediately prior to the above reaction. Finely divided Zn dust (1.0 mole equivalents) was first washed two to four times with 3% hydrochloric acid until the solution was clear and evolved hydrogen gas. The zinc was then washed twice with 18 M-Ohm water. Next, a 2% $CuSO_4$ aqueous solution was added to the freshly add-washed Zn dust and the solution mixed via a magnetic stirrer until it became colorless. The colorless supernatant was decanted and a second volume of 2% $CuSO_4$ solution was added to the Zn dust. This process was repeated several times until the $CuSO_4$ solution remained blue and the Cu—Zn catalyst became a red powder. Finally, the completed Cu—Zn catalyst was rinsed 3-4 times with water, followed by 2-3 methanol rinses. The resulting dark-red powder was then dried under low vacuum for at least 2 hours at 40-50° C.

Chemical Reaction is as follows: 5-ethyl-2-pyridone (≧96%, 1.0 mole equivalents), and potassium carbonate (1.2 mole equivalents) were combined in a 5 liter reaction flask mounted in a heating mantle. Next, the bromobenzene (2.5 mole equivalents) and the Cu—Zn catalyst (0.05 mol equivalents) were added to the flask. A stirring apparatus was attached and the reaction flask flushed with argon gas for several minutes. After adjusting the stirring apparatus, the mixture was heated for 60-90 min. until it refluxed gently under argon for 48-72 hours. Formation of an off-white solid on the side of the flask indicated the start of the reaction. The progress of the reaction was checked by thin layer chromatography (TLC) every 24 hours. When TLC analysis detected no substrate, the stirring apparatus and argon source were removed. After completion of the reaction, un-reacted bromobenzene was removed from the reaction mixture by distillation under high vacuum.

Extraction, filtration and concentration: After allowing the flask to cool for at least 30 min, 0.5-0.6 L of methylene chloride and 10-20 g of Norit were added into the flask and mixed thoroughly. The liquid phase was filtered through a short Celite (diatomaceous earth) column to remove any small particles. This extraction was repeated several times without Norit and the filtrate was pooled in a large flask. The remaining solids left behind were allowed to dry overnight, then pulverized and extracted with $CH_2Cl_2$. The resulting washings were filtered as before.

The pooled filtrates and $CH_2Cl_2$ washings of the Celite column were later filtered through a folded filter paper into a rotary distillation flask. Next, the filtrate solution was distilled under vacuum to remove all $CH_2Cl_2$. The resulting brown viscous solution was then transferred to a Teflon-coated baking pan. The residual viscous solution in the flask was rinsed with ethyl acetate and transferred to the baking pan and then dried overnight or longer at room temperature in the hood to yield a dark-brown solid containing 5-ethyl-1-phenyl-2-(1H)-pyridone (5-EPP).

Re-crystallization and purification: Approximately 100-150 g of crude 5-EPP was dissolved with approximately 100 mL ethyl acetate in a 1000 mL beaker (Beaker-I). Beaker-I was covered with aluminum foil and the contents gently brought to a boil on a hot plate in the hood. After removing the beaker from the heating plate, hexanes were added to the boiling solution while stirring continuously with a Teflon stirring rod. When the upper, hexanes-enriched phase began to separate from the lower phase (ethyl acetate-enriched), all stirring ceased for 5-10 minutes and the solution was allowed to slowly cool and fully separate. The upper phase was clear and had a faint yellow or orange color. The upper phase was gently poured into a second beaker (Beaker-II) and this solution was allowed to settle without stirring for a while (<5 min). As usually happens, a small amount of an oily yellow liquid fell out of solution forming a distinct layer on the bottom of Beaker-II. The upper phase was carefully poured into a Teflon-coated baking pan placed in the hood, leaving the yellow oily contaminant on the bottom of Beaker-II. Beaker-II was rinsed into Beaker-I with ethyl acetate, pooling any residual contents and rinses with the original ethyl acetate solution in Beaker-I. Beaker-I was placed back on the heating plate and the extraction as described above was then repeated. All hexanes-enriched extracts from Beaker-II were transferred into the same baking pan. The process was repeated until the solution volume in Beaker-I was less than 10 mL and became dark and oily. As the hexanes and ethyl acetate solution evaporated from the baking pan, yellow or white crystals of purified 5-EPP formed throughout the pan. A Teflon spatula was used to gently scrape the sides and bottom of the pan and to mix the crystallized contents. Following thorough extraction of the Beaker-I contents, the pan contents were left in the fume hood for 15-30 minutes to allow some of the solvent to evaporate. The pan contents were intermittently mixed and scraped to allow for continuous contact between the crystalline material and the liquid phase. When the liquid level had been reduced by one-third to one-half, the remaining liquid was poured off into a 1 L beaker and the remaining crystals left in the hood to dry for several hours.

Yields exceeding 90% have been achieved after one round of re-crystallization. When the 5-EPP is not sufficiently pure after one round of re-crystallization as judged by color of 5-EPP, visible oily contaminants, or TLC analysis, then the re-crystallization process can be repeated. Yield of this process ranged from 65-80%. After the purified solid was dried overnight at room temperature, the described process yielded a fine white crystalline powder with melting point of 55-59° C. Reverse phase high-performance liquid chromatography (HPLC) analysis and nuclear magnetic resonance (NMR) confirmed this material contained >99% 5-ethyl-1-phenyl-2-(1H)-pyridone of the structure shown in FIG. 3.

It has been found that 5-ethyl-1-phenyl-2-(1H)-pyridone ("5-EPP") may be administered to mammals for treatment of sepsis. Sepsis is a medical condition caused by infection of the blood or tissues of a mammal by microorganisms such as bacteria, viruses, or fungi. Septicemia is a term often used to indicate rampant infection of the body, detectable in the bloodstream. If left untreated, sepsis can lead to serious complications or death.

5-ethyl-1-phenyl-2-(1H)-pyridone can be administered to a mammal in need of treatment for sepsis or infection due to microorganisms. Appropriate routes of administration are by injection (intravenous (i.v), intraperitoneal (i.p.), intramuscular (i.m.)), orally or by any other route which allows the compound to enter the bloodstream. Preferably, it is administered i.v., i.p. or orally. The 5-ethyl-1-phenyl-2-(1H) pyridone is preferably formulated in a pharmaceutical carrier appropriate for the route of administration. Preferably, a pharmaceutical carrier for 5-ethyl-1-phenyl-2-(1H)-pyridone for injection is selected from isotonic saline and propylene glycol and combinations thereof. Most preferably, 5-EPP is added to isotonic saline at a concentration of 20 mg/mL or less to form a colorless composition at room temperature.

It has been found that an effective amount of 5-ethyl-1'-phenyl-2-(1H)-pyridone to treat sepsis ranges from 5 mg/kg body weight to about 200 mg/kg body weight per day, preferably 10 mg/kg body weight to 40 mg/kg body weight per day. Most preferred for non-oral routes of administration is about 10-25 mg/kg body weight per day The effective amount can be given once per day or in multiple doses. In a preferred embodiment, a single dose is given by iv infusion once per day. The effective amount has been found to block the lethal effects of septic shock in mammals.

The compound, 5-ethyl-1-phenyl-2-(1H)-pyridone, may also be provided in an oral total dose form either in tablets or capsules (or otherwise in combination with a pharmaceutical carrier which is suitable for oral administration to an animal) to provide a dose ranging from 5 mg/kg body weight to 200 mg/kg body weight per day, preferably 10 mg/kg body weight to 80 mg/kg body weight per day and most preferred 20 to 50 mg/kg body weight per day. Preferably, the oral dosage is administered in divided dosages. Most preferably, the oral dosage is administered in three (3) daily doses at intervals of 8 hours.

The sepsis syndrome is a complex illness that results from a systemic host response to a variety of insults, particularly infection, which is manifested by varying degrees of hypotension, coagulopathy, and multi-organ dysfunction. Pathophysiologic events occur in early and late phase responses. Early responses in sepsis are characterized by the release of a number of proinflammatory mediators including tumor necrosis factor-alpha, interleukine-6 and interleukine-12 (Dinarello C A. Chest 2000; 118:503-508). Methods for evaluating the protective effects of 5-ethyl-1-phenyl-2-(1H)-pyridone (5-EPP) against multi-organ dysfunction, and the serum levels of proinflammatory cytokines and the mortality in several animal models of sepsis are described. It is herein disclosed that 5-EPP can be used as a treatment agent in mammals for septic shock.

Example 1

Use of 5-ethyl-1-phenyl-2(1H)-pyridone (5-EPP) to Block Lethal Shock Caused by Lipopolysaccharide (LPS) and D-Galactosamine Mice were treated with 5-EPP after inducing shock with lipopolysaccharide (LPS) pursuant to established models for lethal LPS-induced shock. The method described by Galanos C, Freudenberg M A, Reutter W. Proc Natl Acad Sci USA. 1979 November; 76 (11):5939-43 was followed. The survival of the mice after treatment with various doses of the agent in LPS/D-galactosamine model of septic shock was monitored. All agents were injected simultaneously via the intraperitoneal route and the response compared to a placebo agent (saline).

All data were analyzed by Fisher's exact test (Prism™ for Window 4.02, Graphpad Software, Inc., San Diego, Calif.). A value of $P<0.05$ was considered to be statistically significant.

Table 1 clearly illustrates that 5-ethyl-1-phenyl-2(1H)-pyridone (5-EPP) protected mice from lethal LPS/D-galactosamine-induced shock at 72 hrs post-treatment.

TABLE 1

| Group | Treatment | Result | (N) | P-value |
|---|---|---|---|---|
| I | Saline Control | 54% mortality | (21) | |
| II | 25 mg/kg 5-EPP | 30% mortality | (20) | 0.1277 |
| III | 50 mg/kg 5EPP | 5% mortality | (20) | 0.001 |
| IV | 100 mg/kg 5-EPP | 0% mortality | (20) | <0.001 |

Mortality in control mice occurred within 24 hours after treatment, while deaths in the treatment groups occasionally occurred beyond this time point, particularly in the 25 mg/kg group. We therefore disclose that higher doses of 5-EPP offer a significant level of protection and complete protection at the highest dose against LPS/D-galactosamine-induced septic shock and delay of the onset of lethal shock at the lowest dose.

Example 2

Use of 5-ethyl-1-phenyl-2(1H)-pyridone (5-EPP) to Block Lethal Shock Caused by Lipopolysaccharide (LPS) and D-Galactosamine The methodology utilized in Example 1 was used to treat rats. Juvenile Sprague-Dawley rats were induced with LPS/D-galactosamine-septic shock. The animals were monitored for 66 hours after treatment and the resulting data analyzed by the same statistical tests and criteria as in Example 1. As shown in Table 2, 5-EPP also prevented development of lethal shock in rats.

TABLE 2

| Group | Treatment | Result | (N) | P-value |
|---|---|---|---|---|
| I | Saline Control | 100% mortality | (8) | |
| II | 75 mg/kg 5-EPP | 14.3% mortality | (7) | <0.011 |
| III | 200 mg/kg 5-EPP | 12.5% mortality | (8) | <0.001 |

The data in Table 2 demonstrates that in this rat model of septic shock, mortality in both the control group and drug-treated groups occurred within the first 42 hours after treatment. Although a clear dose-response effect for 5-EPP is not observed in this data, the results are entirely consistent with those from the mouse experiments since they confirm that 5-EPP can protect mammals from endotoxin-induced septic shock.

Example 3

Use of 5-ethyl-1-phenyl-2(1H)-pyridone (5-EPP) to Block Lethal Shock Caused by Lipopolysaccharide (LPS) Alone The survival of mice subjected to treatment of the agent and LPS alone pursuant to the methodology of Galanos C, Freudenberg M A, Reutter W. *Proc Natl Acad Sci USA*. 1979 November; 76 (11)5939-43) was observed. This procedure is believed to evoke a pathophysiological response which is more like that observed during septic shock than that caused by the LPS and galactosamine.

All agents were injected simultaneously via the intraperitoneal route and the response compared to a placebo agent (saline).

The animals were monitored for 4 days after treatment and the resulting data analyzed by the same Fisher exact test and criteria as before. As shown in the Table 3, 5-EPP partially prevented development of lethal shock in mice treated with LPS alone (30 mg/kg).

TABLE 3

| Group | Treatment | Result | (N) | P-value |
|---|---|---|---|---|
| I | Saline Control | 100% mortality | (11) | |
| II | 100 mg/kg 5-EPP | 30% mortality | (10) | P < 0.01 |

All deaths in both control and 5-EPP groups were observed by the 42 hr time point. A significant protective effect of 5-EPP against LPS-induced septic shock was found.

Example 4

Use of 5-ethyl-1-phenyl-2(1H)-pyridone (5-EPP to Block Increased Levels of Various Serum Biomarkers as an Index of Multi-Organ Dysfunction in Cecal Ligation and Puncture (CLP) Model of Sepsis Cecal ligation and puncture (CLP) is a more advanced model of septic shock than those involving lipopolysaccharide (LPS). In this model, as described by Wichterman K A, Baue A E, Chaudry I H (J Surg Res. 1980, 29; 189-201), mice are given intraperitoneal (IP) injections of the test compound or saline (control) prior to the beginning of the surgery. The mice are then anesthetized and a laparotomy is performed. The cecum is isolated and separated from the rest of the intestines by tying it at its base with a suturing thread. The cecum is then punctured with a needle. This facilitates influx of the colonic microflora into the abdominal cavity, which results in polymicrobial-induced peritonitis. Unlike the endotoxin model of septic shock, which is initiated by purified bacterial cell wall products, lipopolysaccharide (LPS), that simulates an acute septic shock, the CLP model more closely mimics clinically encountered signs of septic shock seen in humans as it is triggered by living bacteria.

Alteration of serum biomarkers is a proven index of general morbidity and specific organ dysfunction. For example, increases in serum alanine transaminase (ALT) generally indicate liver dysfunction, blood urea nitrogen (BUN) for kidney dysfunction, and creatine kinase for muscle damage and kidney dysfunction. The serum glucose levels are frequently altered during septic shock.

Male Swiss-Webster mice, seven weeks old, were injected with 5-EPP (200 mg/kg) or saline (control) by intraperitoneal route two hours prior to the beginning of the surgery. They were anesthetized by a mixture of xylazine and ketamine, and a laparotomy was performed. The cecum was separated from the rest of the intestine, ligated with suture, and then punctured with an 18 gauge needle. Blood was collected by cardiac puncture 3, 6, or 12 hours after CLP and the serum isolated by centrifugation. Analysis of serum transaminases, blood urea nitrogen, creatine kinase, and glucose was carried out by a commercial company (Idexx Laboratories, West Sacramento, Calif.).

The results are reported as the mean±standard error of the mean with the number of animals in parentheses for each group. The statistical analysis for differences between saline control and 5-EPP pretreated mice was performed using Fisher exact test (Prism™ for Windows 4.02, Graphpad Software, Inc., San Diego, Calif.). A value of $P<0.05$ was considered to be the minimum level of statistical significance. Reference values were determined by analyzing serum from mice injected with saline but not subjected to the CLP procedure.

The following Tables clearly illustrate that pretreatment with 5-EPP (200 mg/kg, ip) partially reversed the CLP-induced increases in several septic shock-related serum biomarkers and hemodynamic imbalance compared to saline-CLP control.

TABLE 4

Effects of pretreatment with 5-EPP on the serum level of alanine transaminase (ALT) as an index of liver dysfunction in the CLP model of sepsis.

| Treatment Group | 3 Hours Post-CLP | 6 Hours Post-CLP | 12 Hours Post-CLP |
|---|---|---|---|
| Saline Control | 109.3 ± 10.8 (11) | 170.1 ± 24.0 (10) | 159.0 ± 36.2 (10) |
| 200 mg/kg 5-EPP | 159.1 ± 21.2 (11) | 128.9 ± 28.7 (12) | 148.2 ± 12.5 (12) |
| P-Value | >0.05 | >0.05 | >0.05 |

(Reference Range = 28.2-35.8 U/L)

While the differences in ALT values were not statistically significant between saline and 5-EPP groups, there was a trend of reduction in this biomarker in 5-EPP pretreated mice.

TABLE 5

Effects of pretreatment with 5-EPP on the level of blood urea nitrogen (BUN) as an index of kidney dysfunction in the CLP model of sepsis.

| Treatment Group | 3 Hours Post-CLP | 6 Hours Post-CLP | 12 Hours Post-CLP |
|---|---|---|---|
| Saline Control | 28.2 ± 2.0 (11) | 34.5 ± 3.1 (10) | 52 ± 1.0 (10) |
| 200 mg/kg 5-EPP | 20.8 ± 0.1 (11) | 19.4 ± 1.0 (12) | 23 ± 2.3 (12) |
| P-Value | <0.05 | <0.001 | <0.001 |

(Reference Range: (16.2-18.5 mg/dL)

Increases in BUN are routinely used as an index of kidney dysfunction in clinical settings. Pretreatment with 5-EPP significantly decreased the CLP-induced increases in BUN at all times of the measurement. In fact, the levels in the 5-EPP pretreated mice almost fell within the range of the reference values.

TABLE 6

Effects of pretreatment with 5-EPP on the serum level of creatine kinase as an index of muscle and kidney damage in the CLP model of sepsis

| Treatment Group | 3 Hours Post-CLP | 6 Hours Post-CLP | 12 Hours Post-CLP |
|---|---|---|---|
| Saline Control | 3235.5 ± 306.5 (11) | 2837.8 ± 355.9 (9) | 3432.6 ± 427.1 (9) |
| 200 mg/kg 5-EPP | 2790.4 ± 370.8 (11) | 1950.3 ± 244.1 (12) | 778.5 ± 91.6 (12) |
| P-Value | >0.05 | >0.05 | <0.001 |

(Reference Range: (62.5-185.7 U/L)

Pretreatment with 5-EPP decreased the CLP-induced increases in the serum level of creatine kinase at all three time points. However a significant decrease was only observed at 12 hours after CLP.

TABLE 7

Effects of pretreatment with 5-EPP on the serum level of glucose in the CLP model of septic shock

| Treatment Group | 3 Hours Post-CLP | 6 Hours Post-CLP | 12 Hours Post-CLP |
|---|---|---|---|
| Saline Control | 539.9 ± 23.7 (10) | 202.2 ± 15.0 (9) | 104.5 ± 8.5 (10) |
| 200 mg/kg 5-EPP | 303.9 ± 30.8 (11) | 116.7 ± 7.7 (12) | 102.9 ± 5.9 (12) |
| P-Value | <0.001 | <0.001 | >0.05 |

(Reference Range: 62-175 mg/dL)

Pretreatment with 5-EPP caused highly significant decreases in the CLP-induced increases in the serum levels of glucose at 3 hr and 6 hr post-treatment. Glucose levels in both treatment groups returned to reference level at 12 hr post-CLP.

TABLE 8

Effects of pretreatment with 5-EPP on the recoverable blood-serum volume as an indication of hemodynamic imbalance in the CLP model of sepsis

| Treatment Group | 3 Hours Post-CLP | 6 Hours Post-CLP | 12 Hours Post-CLP |
|---|---|---|---|
| Saline Control | 198.5 ± 21.52 (13) | 161.9 ± 13.87 (13) | 159.6 ± 16.18 (14) |
| 200 mg/kg 5-EPP | 238.8 ± 20.11 (13) | 219.6 ± 16.70 (12) | 282.7 ± 27.70 (13) |
| P-Value | >0.05 | <0.05 | <0.001 |

Average volume (microliter) of Serum

The volume of serum obtained from blood of saline-pretreated CLP mice was consistently lower than that of 5-EPP-pretreated CLP mice. Although there was no significant difference at 3 hr, the serum volume was significantly higher in 5-EPP pretreated mice than the saline control both at 6 and 12 hour after the CLP.

Since there was no significant difference in the serum to blood ratio (data not shown) between the two groups at any time, this indicates that the animals in both groups were similarly hydrated; and this difference may be partly accounted for by the ability of 5-EPP to prevent the degree of hemodynamic imbalance resulting from septic shock in the saline-control CLP mice.

Example 5

Use of 5-ethyl-1-phenyl-2-pyridone to Block Increased Serum Levels of Alanine Transaminase, Aspartate Transaminase, and Proinflammatory Cytokines in Lipopolysaccharide/D-Galactosamine Model of Septic Shock Mice were treated simultaneously with LPS (10 μg/kg) and D-galactosamine (600 mg/kg) (Galanos C, Freudenberg M A, Reutter W. Proc Natl Acad Sci USA. 1979, 76 (11):5939-43) and 5-EPP (200 mg/kg) by intraperitoneal route in a separate set of experiments. They were anesthetized with halothane and blood was collected at different times by cardiac puncture and centrifuged to separate serum. The serum levels of alanine transaminase (ALT) and aspartate transaminase (AST) were measured by a commercial diagnostic company (Idexx Laboratories). The serum levels of tumor necrosis factor-alpha (TNF-α), interleukin-6 (IL-6) and interleukin-12 (IL-12) were determined by commercially available mouse enzyme-linked immunosorbent assay (ELISA) kits (BD Bio-Sciences, San Jose, Calif.).

The methodology utilized in Example 4 was used to measure and analyze the serum enzyme data for statistical significance. The serum levels of proinflammatory cytokines between the 5-EPP treated and saline control groups were analyzed for statistical significance by one-way ANOVA and a Tukey's multiple comparison test (Prism™ for Windows 4.02, Graphpad Software, Inc. San Diego, Calif.).

As shown in Tables 9 and 10, 5-EPP caused a highly significant reduction in the elevated serum levels of ALT and AST at 6 hours and 12 hours after LPS/D-galactosamine treatment, respectively. However, at 3 hours 5-EPP caused a significant increase in both transaminases as compared to saline control group.

TABLE 9

Effects of 5-EPP on the serum level of alanine transaminase (U/L) in the LPS/D-galactosamine model of sepsis

| LPS/D-galactosamine | Saline | N | 5-EPP | N | P-Value |
|---|---|---|---|---|---|
| After 3 Hours | 67.5 ± 2.5 | (8) | 109.4 ± 6.1 | (8) | <0.05 |
| After 6 Hours | 1415.9 ± 685.9 | (7) | 130.0 ± 8.9 | (8) | <0.001 |
| After 12 Hours | 1177.2 ± 622.8 | (5) | 109.5 ± 8.3 | (8) | <0.001 |

TABLE 10

Effects of 5-EPP on the serum level of aspartate transaminase (U/L) in the LPS/D-galactosamine model of sepsis

| LPS/D-galactosamine | Saline | N | 5-EPP | N | P-Value |
|---|---|---|---|---|---|
| After 3 Hours | 69.1 ± 3.5 | (8) | 131.3 ± 11.9 | (8) | <0.01 |
| After 6 Hours | 657.6 ± 276.4 | (7) | 152.38 ± 14.4 | (8) | <0.001 |
| After 12 Hours | 577.2 ± 212.0 | (5) | 173.38 ± 13.0 | (8) | <0.001 |

The increased levels of serum alanine transaminase and aspartate transaminase are clinically used as a diagnostic biomarker for liver dysfunction, which is generally encountered in cases of septic shock in humans. The findings of the present studies that treatment with 5-EPP dramatically reduced the elevated levels of both transaminases at 6 hours and 12 hours in the LPS/D-galactosamine model of septic shock in mice suggest the protective effect of 5-EPP against liver damage caused by sepsis.

Use of 5-EPP significantly reduced the LPS/D-galactosamine-induced increases in the serum levels of TNF-α (Table 11), IL-6 (Table 12), and IL-12 (Table 13) at 90 minutes after the treatment in a dose dependent manner.

TABLE 11

Effects of 5-EPP on the serum level of TNF-α in LPS/D-galactosamine model of sepsis

| Group | Value | N | P-value |
|---|---|---|---|
| Group I - saline control | 11,200 ± 2100 pg/mL | (9) | P-value |
| Group II - 12.5 mg/kg | 5,220 ± 1280 pg/mL | (8) | P < 0.01 |
| Group III - 25 mg/kg | 2,780 ± 481 pg/mL | (10) | P < 0.001 |
| Group IV - 50 mg/kg | 576 ± 79 pg/mL | (8) | P < 0.001 |
| Group V - 100 mg/kg | 340 ± 34 pg/mL | (8) | P < 0.001 |

TABLE 12

Effects of 5-EPP on the serum level of IL-6 in the LPS/D-galactosamine model of sepsis

| Group | Value | N | P-values |
|---|---|---|---|
| Group I - saline control | 12,474 ± 646 pg/mL | (7) | P-values |
| Group II - 50 mg/kg | 9,980 ± 564 pg/mL | (6) | <0.05 |
| Group III - 100 mg/kg | 5,111 ± 343 pg/mL | (7) | <0.001 |
| Group IV - 200 mg/kg | 3,578 ± 421 pg/mL | (7) | <0.001 |

TABLE 13

Effects of 5-EPP on the serum level of IL-12 in the LPS/D-galactosamine model of sepsis

| Group | Value | N | P-value |
|---|---|---|---|
| Group I - saline control | 7,101 ± 307 pg/mL | (7) | P-value |
| Group II - 50 mg/kg | 2,809 ± 325 pg/mL | (6) | <0.001 |
| Group III - 100 mg/kg | 1,371 ± 124 pg/mL | (7) | <0.001 |
| Group IV - 200 mg/kg | 870 ± 99 pg/mL | (7) | <0.001 |

Example 6

Use of 5-ethyl-1-phenyl-2(1H)-pyridone (5-EPP) on Secreted and Cell-Associated TNF-α In Vitro in Human Monocytic Cells The effects of 5-EPP on secreted and cell associated TNF-α was examined in vitro using phorbol myristate acetate-transformed (PMA; Sigma, St. Louis, Mo.) human monocytic cells, THP-1 (ATCC, Manassas, Va.) according to the technique described by Grattendick et al. (International Immunopharmacology 2008, 8; 679-87). Briefly, cells were incubated for 3 hr on 96-well plates with culture media, 1 ng/mL LPS, or 1 ng/mL LPS 0-200 µg/mL 5-EPP before culture media were collected and analyzed for the presence of secreted TNF-α via a commercially available enzyme-linked immunosorbent assay (ELISA) kit (BD Biosciences, San Diego, Calif.). Separately, identically treated cells were lysed and their cell-associated TNF-α levels were determined via ELISA. All treatment groups were simultaneously compared using one-way ANOVA and Tukey's multiple comparison tests.

As shown in Table 14, use of 5-EPP reduced significantly (P<0.001) both secreted and cell-associated TNF-α in a dose dependent manner as compared with the 0 µg/mL control. The values are expressed in pg/mL as mean±standard error of the mean for four replicates at all concentrations in each case.

TABLE 14

Effects of 5-EPP on secreted and cell-associated TNF-α on THP-1 cells exposed to LPS in vitro

| | Concentration of 5-EPP | | | | |
|---|---|---|---|---|---|
| | 0 µg/mL | 10 µg/mL | 33 µg/mL | 100 µg/mL | 200 µg/mL |
| Secreted TNF-α | 8791.6 ± 185.9 | 5382.8 ± 91.8 | 3261.5 ± 94.1 | 2073.7 ± 60.7 | 1469.7 ± 58.9 |
| Cell-associated TNF-α | 74.4 ± 7.5 | 35.4 ± 3.1 | 25.9 ± 1.6 | 19.0 ± 0.9 | 10.1 ± 1.3 |

Cytotoxicity analysis was performed on THP-1 cells treated with various concentrations of 5-EPP using the MTS (3-(4,5-dimethylthiazol-2-yl)-5-(3-carboxymethoxyphenyl)-2-(4-sulfophenyl)-2H-tetrazolium, inner salt) assay (Promega, Madison, Wis.). This was necessary to prove the reduced TNF-α observed in 5-EPP-treated cells was not due to cell death. Cells were treated with LPS (1 ng/mL) and 5-EPP (0-500 μg/mL) for 12 hours and showed no cytotoxicity until they were exposed to at least 300 μg/mL of 5-EPP.

Example 7

Use of 5-ethyl-1-phenyl-2(1H)-pyridone (5-EPP) on LPS/D-Galactosamine-Induced Mortality The effects of treatment with 5-EPP on LPS/D-galactosamine-induced mortality was investigated in mice. At least 10 mice in each group were challenged with either a lethal dose of LPS (20 μg/kg) and D-galactosamine (600 mg/kg) or the same dose of LPS/D-galactosamine+different doses of 5-EPP by intraperitoneal route and the morality in each group was monitored at different times for 4 days in order to evaluate the protective effects of 5-EPP against LPS/D-galactosamine-induced mortality.

Figure 2:
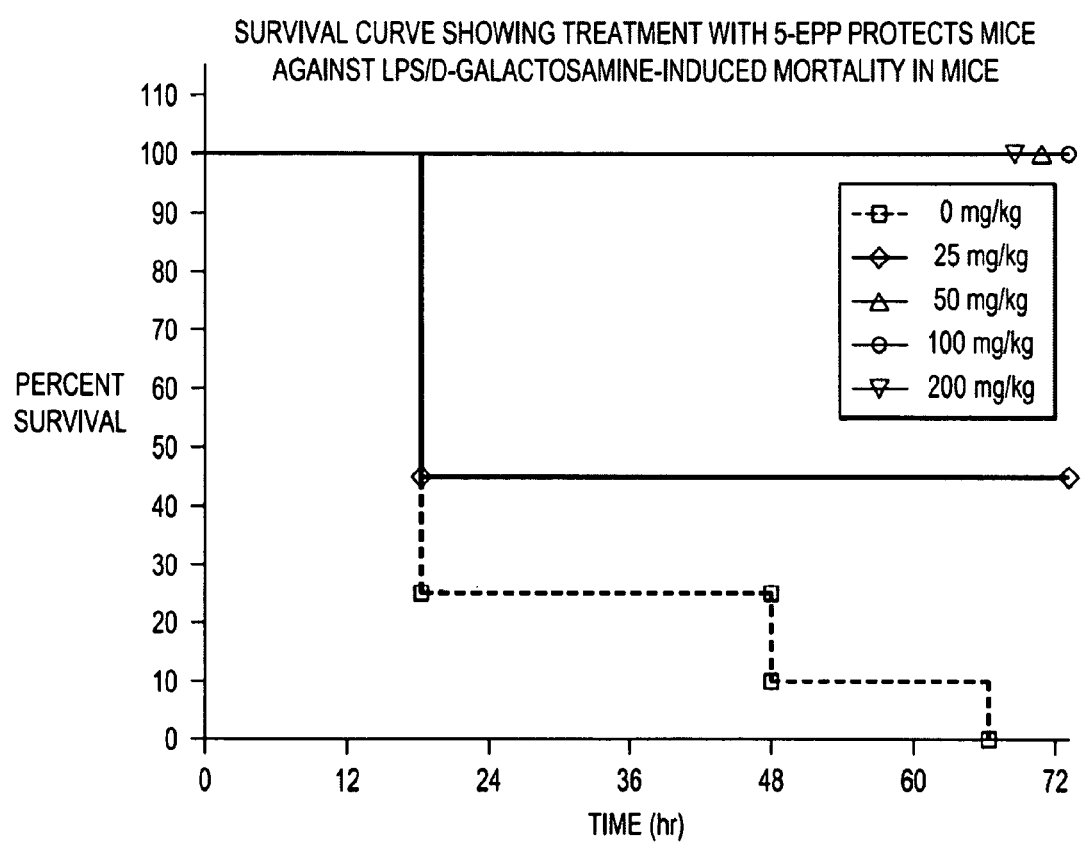
FIG. 2 is graph depicting a survival curve for mice in LPS/D-galactosamine model of sepsis treated with 5-ethyl-1-phenyl-2-(1H)-pyridone (5-EPP).

FIG. 2 clearly demonstrates that 20 μg/kg LPS and 600 mg/kg D-galactosamine caused 100% mortality before 72 hours after the treatment. However, the survival of mice treated with 25 mg/kg of 5-EPP was 45% and 100% at 50 mg/kg, 100 mg/kg and 200 mg/kg with $p \leq 0.0001$ as determined by Chi square test.

Example 8

Determination of $LD_{50}$ Estimate after a Single Dose of 5-ethyl-1-phenyl-2(1H)-pyridone (5-EPP)

Male Swiss-Webster mice were obtained from standard commercial sources at 7 weeks of age, housed in the laboratory for at least 1 week prior to use and were provided standard mouse chow and water ad libitum. Animals were subjected to a 12 hour/12 hour light-dark cycle.

Six groups of mice were injected via the intraperitoneal route with 5-EPP (250-500 mg/kg) dissolved in sterile isotonic saline, immediately replaced in their cages and then observed carefully for the next 6-8 hours. A $LD_{50}$ value was estimated from the mortality data by a non-linear curve fitting program (Prism™ for Windows 4.02).

Ataxia, loss of the righting reflex and labored breathing were observed within 5 minutes at the highest doses (450-500 mg/kg), with death occurring within 10-60 minutes post-injection. Animals exposed to lower doses appeared to cycle between states of hyperactive grooming, walking and grooming and a state of apparent stupor. Symptoms at these doses gradually lessened over 1-2 hours to a point where the animals appeared unaffected and resumed normal levels of activity.

Non-linear curve fitting to a sigmoidal dose-response curve yielded a $LD_{50}$ value of 380 mg/kg (log 2.581 with a standard error of log 0.03367) with $R^2=0.949$. The raw mortality data demonstrated a $LD_{100}=450-500$ mg/kg. Furthermore, the rapid onset of symptoms which were observed here and in other related studies suggest that 5-EPP is rapidly absorbed and distributed across the blood-brain barrier when administered by the intraperitoneal route.

Example 9

Solubility of 5-ethyl-1-phenyl-2(1H)-pyridone (5-EPP)

5-EPP is soluble in both water and saline at 20 mg/mL at room temperature, forming colorless and absolutely clear solutions. Thus, 5-EPP can be formulated in isotonic solution for I.V. infusion. This compound appeared to be equally soluble in either water or saline. Higher concentrations of the compound ($\geqq 30$ mg/mL) do not completely dissolve and may form a faint residue on polystyrene test tubes.

All solutions were prepared by weighing the chemical, transferring his solid into a polypropylene tube or polystyrene tube and then adding either water or saline to the final desired volume. The compound was dissolved by intermittent mixing with a vortex mixer, gentle heating in a warm water bath (40-45° C.) and sonication (3×15 min.).

Once the solid had completely dissolved, no precipitation was observed after returning to room temperature. Even after standing at room temperature overnight or following refrigeration, no precipitation was observed.

The pH of two freshly prepared solutions of the compound each at 20 mg/mL concentration was measured with a calibrated Mettler MP-220 pH meter equipped with a pH electrode (model 413). The pH of the solution made in water averaged 7.4 as compared to solutions made in isotonic saline in which the pH averaged 6.21 using triplicate samples in each case, as shown in the table below.

TABLE 15

Solubility of 5-EPP in Distilled Deionized Water and Isotonic Saline

| Solvent | Volume added (mL) | 5-EPP (mg) | Final 5-EPP mg/mL | Results | pH |
| --- | --- | --- | --- | --- | --- |
| DI Water | 10 | 0 | 0.0 | | 7.56 |
| DI Water | 10.1 | 202.1 | 20.0 | soluble | 7.24 |
| DI Water | 10.1 | 202.1 | 20.0 | soluble | 7.29 |
| Isotonic saline | 10 | 0 | 0.0 | | 6.27 |
| Isotonic saline | 10 | 201.3 | 20.1 | soluble | 6.20 |
| Isotonic saline | 10 | 200.1 | 20.0 | soluble | 6.13 |

Example 10

Synthesis and Purification of 5-ethyl-1-phenyl-2(1H)-pyridone (5-EPP)

In a preferred embodiment of the synthesis method the following exemplary method was performed. A mixture of 3-ethyl pyridine (2.0 kg), oleic acid (1.8 mL) and $NaNH_2$ (878.7 g in a 50 wt % mixture in toluene) were combined in a Parr 20 Liter stainless steel bomb reactor (Model 4555M stirred five gallon, stainless steel reactor with A 1760HC Series Master Control from Parr Instrument Company, Moline, Ill.).

Once the reactor was sealed and connected to 2 gas sources, the reactor motor was started to stir the mixture. The gas outlet port was closed, and the reactor was pressurized initially to 30 psi with ammonia gas and then to 200 psi with nitrogen gas before the inlet port is closed. Concurrently, a flow of coolant water was circulated to cool the stirring motor and to allow control of the reactor temperature. The reactor was heated gradually to a maximum of 180° C. over 90 minutes. Generated hydrogen gas was vented when the reactor pressure rose above 320 psi.

Hydrogen gas production ceased after approximately 4.5 hours indicating that the reaction had ceased. At this time, the reactor temperature control was reset to 30° C. to allow continuous cooling of the reactor and the sealed reactor was allowed to cool overnight with stirring. Subsequent to reactor decompression, 3 liters of reagent grade water was added to the reactor. The reactor was promptly resealed and allowed to cool overnight.

On the third day, the stirring and cooling systems were shut off for two hours to permit phase separation of the reaction mixture. A heavier aqueous phase was removed via a valve located at the bottom of the reactor and extracted once with 0.5 liters of toluene. This toluene extract was added back to the original organic phase and the resulting mixture was dried over anhydrous magnesium sulfate ($MgSO_4$).

The $MgSO_4$ was removed from the toluene phase by gravity filtration. Subsequently, the toluene was removed under vacuum via a rotary evaporator. This process yielded approximately 2.2 liters of a crude dark brown liquid, comprising the reaction product.

Thereafter, the crude dark brown liquid recovered from the initial Chichibabin reaction was distilled under vacuum in 500 mL batches through a 60 cm Vigreaux distillation column in order to isolate and concentrate distillates of the desired 2-amino-5-ethyl pyridine isomer. Each distillation batch was repeated at column temperatures ranging from 85-105° C. Each fraction contained at least 85% of the 2-amino-5-ethyl pyridine isomer, as determined by reverse phase HPLC and these fractions were pooled.

Approximately 300 g of the synthetic concentrate of 2-amino-5-ethyl pyridine (>88% by HPLC) in 20% sulfuric acid ($H_2SO_4$, wt/vol) in reagent grade water was chilled thoroughly in an ice bath located in a fume hood. While the mixture was stirred constantly, an aqueous 30% sodium nitrite ($NaNO_2$, wt/vol, 1.2 mole equivalents) solution was added over 4-5 hours.

After completing the addition of the $NaNO_2$ solution, $Na_2CO_3$ (2.0 mole equivalents) was carefully added to the reaction mixture until a pH=8-8.5 was attained. This resulting reaction mixture was then separated into two phases: a dark yellow upper organic phase and a lower light yellow aqueous phase. The mixture was transferred into a reparatory funnel and the two phases were then separated.

After the separation, the aqueous phase was extracted three times with methylene chloride ($CH_2Cl_2$, 800 mL×3). All three $CH_2Cl_2$ phases were pooled with the original organic phase and the resulting pooled mixture was dried over anhydrous $MgSO_4$ overnight. After removing the $MgSO_4$ by gravity filtration, the $CH_2Cl_2$ was removed by rotary evaporation. The resulting material was dried under vacuum to obtain a light yellow solid. This reaction had an approximate yield of 87%.

Catalyst: A copper-zinc (Cu—Zn) catalyst was prepared immediately prior to the above reaction. Zinc dust (0.05 mole equivalents) was washed twice with 3% (wt/vol) hydrochloric acid and then washed twice with reagent-grade water. Next, a portion of aqueous 2% copper sulfate ($CuSO_4.5H_2O$, wt/vol) solution was added to the acid-washed zinc dust and the contents were mixed thoroughly by shaking until the liquid phase became colorless. The colorless solution was decanted off and a second portion of 2% $CuSO_4$ solution added to the zinc dust before the mixture was shaken again. This process was repeated until the $CuSO_4$ solution remained blue, and the grey zinc dust turned into a red powder. Next, the completed Zn—Cu catalyst was filtered and then washed several times with purified water, followed by multiple methanol rinses. The resulting dark-red powder was then dried under vacuum for at least two hours.

A solution of 5-ethyl-2-pyridone (~300 g, 1.0 mole equivalents) in bromobenzene (2.5 mole equivalents) was prepared and the Zn—Cu catalyst (0.05 mole equivalents) and potassium carbonate (1.2 mole equivalents) added.

This reaction mixture was then refluxed gently under argon. The reaction progress was checked frequently by thin layer chromatography (TLC) every 24 hours. When the reaction was complete, un-reacted bromobenzene was removed from the reaction mixture by distillation under high vacuum.

Purification procedure: The remaining solution was extracted three times with $CH_2Cl_2$ (2 L×3) to isolate 5-ethyl-1-phenyl-2-(1H)-pyridone. Each extract was vacuum-filtered through a short Celite (diatomaceous earth) column to remove any small particles. After pooling all of the $CH_2Cl_2$ washings into one vessel, 40 g of activated charcoal was added, and the solution was brought to a boil at approximately 40° C. After boiling for 10-15 minutes, the solution was allowed to cool to room temperature before the charcoal was removed by vacuum filtration through a second Celite column.

The volume of filtrate solution was reduced by rotary evaporation to remove remaining traces of $CH_2Cl_2$. Thereafter, the resulting oily concentrate was transferred to a Teflon-coated pan and dried overnight at room temperature in the hood to yield a dark-brown solid containing 5-ethyl-1-phenyl-2-(1H)-pyridone.

Approximately 100 mL ethyl acetate was added to a 1 L glass beaker (Beaker-I) containing 200 g of the dark-brown solid isolated in the Teflon-coated pan. Beaker-I was placed on a hot plate in the hood, warmed to dissolve the crude solid and then the ethyl acetate solution was brought to a boil. After removing the beaker from the heating plate, hexanes were added to the boiling solution while the contents were stirred continuously. When the upper (hexanes-rich) phase began to separate from the lower phase (mainly ethyl acetate), all stirring ceased for 5-10 minutes and the two phases were allowed to fully separate. The upper phase appeared clear. However, some runs yielded a faint yellow or orange color.

The upper phase (hexanes-rich) was carefully poured into a second beaker (Beaker-II) and this solution was allowed to cool for several minutes to settle without stirring. The upper phase was carefully transferred to a Teflon-coated pan placed in the fume hood, leaving the yellow oily contaminates on the bottom of Beaker-II.

Figure 3:
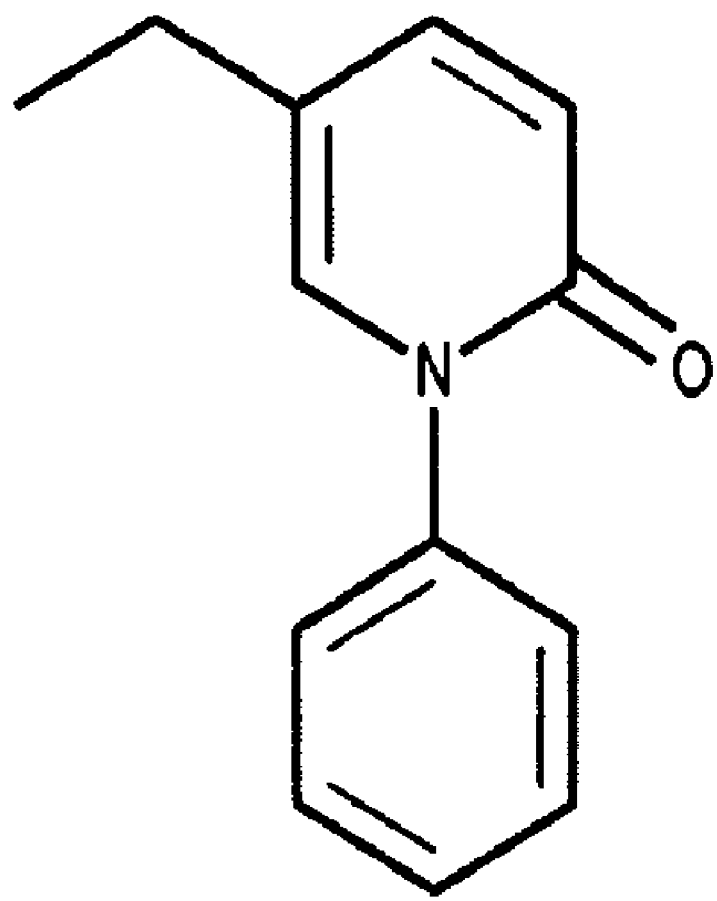
FIG. 3 is a drawing of 5-ethyl-1-phenyl-2-(1H)-pyridone ("5-EPP")

As the combined solutions decanted from Beaker II evaporated, cool yellow or white 5-ethyl-1-phenyl-2-pyridone crystals were formed throughout the pan. Off-white or colored crystals were recrystallized to improve the purity and tested by observation and by TLC. After the purified solid was dried overnight at room temperature, the described process yielded a fine white crystalline powder with a melting point of 57-59° C. Reverse phase HPLC analysis and NMR confirmed this material contained >99% 5-ethyl-1-phenyl-2-(1H)-pyridone as shown in FIG. 3.

Example 11

Treatment of Human Patient in Need of Treatment

A hospitalized patient presents to the Intensive Care Unit for treatment of septic shock.

The septic shock can be the result of bacterial infection acquired during surgical procedures or otherwise, or other etiology. The patient can be treated with an intravenous infusion of purified 5-ethyl-1-phenyl-2-(1H)-pyridone (5-EPP) at (5-40 mg/kg), preferably (10-25 mg/kg).

Example 12

Treatment of Human Patient in Need of Treatment with 5-EPP in Combination with Antibiotics A similar situation as described in Example 11 is presented, however in addition to 5-EPP, the patient is treated with an intravenous infusion of purified 5-ethyl-1-phenyl-2-(1H)-pyridone (5-40 mg/kg), preferably (10-25 mg/kg) in adjunct to intravenous infusion of antibiotics.

Example 13

Treatment of Equine Patient in Need of Treatment with 5-EPP

A horse is diagnosed with colic due to gastrointestinal trauma or infection and can be infused with an intravenous infusion of purified 5-ethyl-1-phenyl-2-(1H)-pyridone (10-25 mg/kg) with or without antibiotics.

Example 14

Inhibition of TNF-α Secretion and TNF-α Associated with Cells

TNF-α associated diseases are treated by administration of 5-ethyl-1-phenyl-2-(1H)-pyridone (10-25 mg/kg) (5-EPP) by iv infusion or other route, This treatment is effective for inhibiting the secretion of TNF-α and the level of TNF-α associated with the cell membrane.

We claim:

1. A method of treating sepsis, consisting of administering an aqueous solution containing an effective amount of 5-ethyl-1-phenyl-2-(1H)-pyridone as a sole therapeutic agent, dissolved in a carrier, by injection into a mammal in need of such treatment, wherein said effective amount is about 5 mg/kg body weight to 100 mg/kg body weight.

2. The method of claim 1, wherein said effective amount is injected into said mammal via a route selected from intravenous, intramuscular, and intraperitoneal.

3. The method of claim 2, wherein said route is selected from intravenous injection and intravenous infusion.

4. The method of claim 1, wherein said effective amount is administered in a single dose.

5. The method of claim 1, wherein said effective amount is administered in multiple doses.

6. A method of treating sepsis, consisting of administering an aqueous solution containing an effective amount of 5-ethyl-1-phenyl-2-(1H)-pyridone as a sole therapeutic agent, dissolved in a carrier wherein said carrier is selected from water and isotonic saline and wherein the concentration of said 5-ethyl-1-phenyl-2-(1H)-pyridone in said solution is from about 20 mg/mL to about 30 mg/mL, and wherein said solution is characterized by being clear at room temperature without any visible precipitate.

7. The method of claim 6, wherein said diluent is water and the pH is about 7.2 to 7.4.

8. The method of claim 6, wherein the diluent is saline and the pH is about 6.1 to 6.3.

9. The method according to claim 4, wherein said one dose comprises a pharmaceutical solution for injection of 5-ethyl-1-phenyl-2-(1H)-pyridone in a concentration providing from about 10 mg/kg to 40 mg/kg to said patient.

10. The method according to claim 4, wherein said one dose comprises a pharmaceutical solution for injection of 5-ethyl-1-phenyl-2-(1H)-pyridone in a concentration providing from about 10 mg/kg to 25 mg/kg to said patient.

11. The method of claim 9, wherein said 5-ethyl-1-phenyl-2-(1H)-pyridone is dissolved in a carrier at room temperature and said concentration is from 20 mg/mL to 30 mg/mL.

12. The method of claim 10, wherein said 5-ethyl-1-phenyl-2-(1H)-pyridone is dissolved in a carrier at room temperature and said concentration is from 20 mg/mL to 30 mg/mL.

* * * * *

UNITED STATES PATENT AND TRADEMARK OFFICE
CERTIFICATE OF CORRECTION

| | | |
|---|---|---|
| PATENT NO. | : 8,093,210 B2 | Page 1 of 1 |
| APPLICATION NO. | : 12/921107 | |
| DATED | : January 10, 2012 | |
| INVENTOR(S) | : Margolin et al. | |

It is certified that error appears in the above-identified patent and that said Letters Patent is hereby corrected as shown below:

Col. 1, Lines 46-47, replace "5-ethyl-1'-phenyl-2-(1H) pyridone" with -- 5-ethyl-1-phenyl-2-(1H) pyridone --
Col. 3, Line 34, replace "add-washed" with -- acid-washed --
Col. 5, Line 12, replace "i.v., i.p. or orally" with -- i.v., i.m., i.p. or orally --
Col. 5, Lines 21-22, replace "5-ethyl-1'-phenyl-2-(1H) pyridone" with -- 5-ethyl-1-phenyl-2-(1H) pyridone --
Col. 6, Line 9, replace "Window 4.02" with -- Windows 4.02 --
Col. 6, Table 1, Row III under "Treatment," replace "5EPP" with -- 5-EPP --
Col. 7, Line 9, replace "Proc Natl Acad Sci USA." with -- (Proc Natl Acad Sci USA. --
Col. 7, Line 10, replace "76 (11)5939-43)" with -- 76 (11): 5939-43) --
Col. 7, Line 36, replace "(5-EPP" with -- (5-EPP) --
Col. 8, Line 11, replace "mean±standard" with -- mean ± standard --
Col. 10, Line 17, replace "5-ethyl-1-phenyl-2-pyridone" with -- 5-ethyl-1-phenyl-2(1H)-pyridone --
Col. 12, Line 36, replace "LPS 0-200" with -- LPS + 0-200 --
Col. 12, Line 50, replace "mean±standard" with -- mean ± standard --
Col. 13, Line 21, replace "LPS/D-galactoseamine+different" with
-- LPS/D-galactoseamine + different --
Col. 14, Line 14, replace "transferring his" with -- transferring this --
Col. 15, Line 44, replace "into a reparatory funnel" with -- into a separatory funnel --
Col. 17, Line 32, replace "route, This" with -- route. This --

Signed and Sealed this
Fifteenth Day of January, 2013

David J. Kappos
*Director of the United States Patent and Trademark Office*